United States Patent [19]

Tham et al.

[11] Patent Number: 5,673,688
[45] Date of Patent: Oct. 7, 1997

[54] ANESTHESIA SYSTEM WITH $CO_2$ MONITOR TO SUPPRESS $CO_2$ BREAKTHROUGH

[75] Inventors: Robert Q. Tham, Madison; James R. Homuth, DeForest, both of Wis.

[73] Assignee: Ohmeda Inc., Liberty Corner, N.J.

[21] Appl. No.: 721,371

[22] Filed: Sep. 26, 1996

[51] Int. Cl.⁶ .................. A61M 16/00; A62B 7/00; A62B 9/00; F16K 31/02
[52] U.S. Cl. ............ 128/204.22; 128/205.13; 128/205.15; 128/205.28; 128/205.23
[58] Field of Search .......... 128/203.12, 203.16, 128/203.25, 203.26, 204.14, 204.18, 204.21, 204.22, 204.28, 205.11, 205.12, 205.13, 205.15, 205.23, 205.28

[56] References Cited

U.S. PATENT DOCUMENTS

| | | | |
|---|---|---|---|
| 3,358,683 | 12/1967 | Goiten | 128/205.23 |
| 3,951,137 | 4/1976 | Conkle et al. | 128/204.22 |
| 4,619,269 | 10/1986 | Cutler et al. | 128/205.12 |
| 4,648,396 | 3/1987 | Raemer | 128/204.22 |
| 4,856,531 | 8/1989 | Meriläinen | 128/205.12 |
| 4,903,693 | 2/1990 | Yasue | 128/205.14 |
| 4,905,685 | 3/1990 | Olsson et al. | 128/204.21 |
| 5,094,235 | 3/1992 | Westenskon et al. | 128/203.12 |
| 5,299,579 | 4/1994 | Gedeon et al. | 128/205.14 |
| 5,315,989 | 5/1994 | Tobia | 128/204.28 |
| 5,320,093 | 6/1994 | Raemer | 128/203.12 |
| 5,471,979 | 12/1995 | Psaros et al. | 128/205.12 |

*Primary Examiner*—Kimberly L. Asher
*Attorney, Agent, or Firm*—Roger M. Rathbun; Salvatore P. Pace

[57] ABSTRACT

A system is provided for detecting the breakthrough of $CO_2$ into the inspiratory limb of a substantially closed circle patient breathing circuit having a $CO_2$ absorber to remove $CO_2$ from the continuously recirculating gases. The $CO_2$ is detected by a gas analyzer located in the inspiratory limb of the patient breathing circuit. Upon detection of that $CO_2$, the system increases the flow of fresh gas into the circle patient breathing circuit to a flow rate in excess of the minute volume of gas being delivered at that time to the patient. The increased flow of fresh gas basically prevents the further flow of $CO_2$ from the expiratory limb into the inspiratory limb, thus preventing the $CO_2$ from being inhaled by the patient.

15 Claims, 1 Drawing Sheet

ANESTHESIA SYSTEM WITH CO₂ MONITOR TO SUPPRESS CO₂ BREAKTHROUGH

BACKGROUND OF THE INVENTION

The present invention relates to anesthesia systems used to provide an anesthetic agent to a patient undergoing an operation.

In general, anesthesia systems are utilized in operating rooms and comprise various equipment necessary to anesthetize the patient and maintain the patient in that state until the operation is completed and it is possible to terminate the introduction of the anesthetic agent.

Such systems comprise various pressure regulators, flow control devices, gas mixing devices and vaporizers to vaporize a volatile liquid anesthetic and to introduce the anesthetic laden gases into the patient. The patient is connected to the system by means of a face mask or other device and which interfaces with the anesthesia system via a patient circuit that may typically have an inspiratory limb through which the gases are introduced into the patient and an expiratory limb that conveys the exhaled gases from the patient.

In one typical anesthesia system, the overall flow of gases to and from the patient may be in a generally closed circuit, commonly referred to as the circle system, that is, the patient is connected to a substantially closed volume supply of gases and rebreathes certain of those exhaled gases supplemented by fresh gas.

As the driving force to the circle breathing circuit, and, of course, to the patient, a ventilator is used and which basically breathes for the patient since the patient is under anesthesia and is unable to carry out the normal spontaneous breathing functions. The ventilator, therefore, provides a quantity of the gas containing a predetermined metered quantity of the anesthetic agent along with other gases such as nitrous oxide and, of course, a life sustaining percentage of oxygen.

That gas containing the anesthetic may be delivered directly by the ventilator into the patient circuit for introduction to the patient or through an intermediate mechanism such as a bellows. In the latter case, the gas from the ventilator does not contain the anesthetic agent but is used to simply power the bellows to collapse that bellows to deliver the aforementioned anesthetic containing gas from the bellows to the patient. Instead of drive gas, other driving means such as an electromechanical or mechanical means are also used. As a further alternative, the patient may be bagged, that is, the clinician may manually manipulate a flexible bag to provide breaths to the patient. In light anesthesia, the patient may also breathe spontaneously into the circle breathing system.

In any of the aforedescribed systems, the anesthetic laden gas is delivered to the inspiratory limb of the circle patient breathing circuit and is introduced into the patient to provide anesthesia to that patient. That anesthetic gas to the inspiratory limb is provided by a source of gases, including fresh gas, oxygen and generally nitrous oxide, that is mixed to a predetermined mixture in a gas mixer and the mixed gases are then passed through an agent vaporizer where the anesthetic agent is introduced into those gases.

In the expiratory limb of the circle patient breathing circuit, as the patient exhales, the exhalation gases pass through the expiratory limb where they are recirculated back to the inspiratory limb where they are again inhaled by the patient. In this manner, the system is closed and which allows the optimum use of the rather expensive anesthetic agent. If the fresh gas added to the circuit exceeds the net of gases taken up by the patient or leaked from the circuit, the excess gases are popped off via a pop-off valve.

Since the patient's exhalation is recirculated, however, there can be a problem in a build up of $CO_2$ that is exhaled by the patient and which is unhealthy for the patient to inhale. Accordingly, in the circle system, the recirculating exhalation gases are passed through a scrubber which is intended to remove $CO_2$ from the gas stream.

The $CO_2$ scrubber or absorber contains an absorbent material, such as sodalime, that absorbs the $CO_2$ and thus removes that $CO_2$ from the gases being recirculated through the circle system. One problem with such systems, however, is that the sodalime ultimately becomes saturated with the $CO_2$ and therefore needs to be replaced periodically so that fresh material may be added to the system. The sodalime generally has an indicator to determine when the absorbent material needs to be replaced, such as change of color, so that the personnel can determine the status of the particular sodalime being used and replace it when necessary.

There are instances, however, that for some reason, the sodalime is not replaced at the proper time or not put in place at all and therefore there is the possibility of a build up of $CO_2$ and which breaks through the absorber and can reenter the inspiratory limb where the harmful $CO_2$ can be inhaled by the patient. Again, as indicated, that inhalation of $CO_2$ is obviously undesirable.

A circle system operating with excess gases being popped off is commonly referred to as a semi-open or semi-closed breathing system. During expiration, the inspiration and expiratory one-way check valves direct patient gases to the expiratory limb of the circuit and deflect fresh gases toward the pop-off valve in the bellows. If the fresh gas added to the circuit exceeds the gases taken up by the patient or leaked from the system, the excess gases are popped off via the pop-off valve. As more and more fresh gas is added to the circle breathing circuit, less of the expired patient gas is recirculated to the patient.

SUMMARY OF THE INVENTION

The anesthesia system of the present invention includes a means of detecting the breakthrough of $CO_2$ from the expiratory limb of the patient circle system into the inspiratory limb and providing protection to the patient against the potential inhalation of $CO_2$.

In particular, the present system provides a means of detecting when the $CO_2$ is present in the inspiratory limb and taking corrective action such as the initiation of an alarm to alert the user and also increasing the fresh gas flow to prevent the recirculation of expired gases through the circle patient breathing system.

In the preferred embodiment, a computer controlled gas blender and vaporizer is utilized and which are capable of metering gases and inhaled anesthetic agent to a circle patient breathing circuit and the ventilator is a computer controlled mechanical ventilator. By the use of an input device, the clinician can establish the desired patient gas and anesthetic agent concentrations.

In the normal course of operation, the user sets the desired inspired concentration of anesthetic and oxygen and communicates that setting to the computer. The computer compares the set values with the agent concentration measured by a gas monitor monitoring the gases in the inspiratory limb of the breathing circuit. The computer thus, in conventional manner, compares the set values with the actual readings of the gases in the inspiratory limb and based on any difference, calculates the appropriate gas flow rates and agent concentration control and provides appropriate signals to the gas blender and the agent vaporizer to deliver and maintain the inspired concentration settings established by the clinician. The remainder of the gases other than oxygen and anesthetic agent is made up by the "balance gas" selected by the user and may typically comprise nitrous oxide although nitrogen (from medical air) or helium are also used.

In the event the gas monitor detects $CO_2$ in the inspiratory limb or in the inspiratory phase of the respired patient gases, the computer first verifies that the presence of $CO_2$ is not intended, that is, the presence of $CO_2$ could be the result of adding $CO_2$ to the fresh gas supplied to the overall system or the absorber may be deliberately bypassed by a bypass valve. In the case of the former condition, the computer checks the gas mixer to see if $CO_2$ is being added to the system and in the case of the latter, the computer checks the state of the bypass valve for the absorber to determine its position.

If the presence of the $CO_2$ in the inspiratory limb cannot be explained as caused by a known, deliberate condition by the computer, the computer will activate an alarm, visual and/or aural to alert the user to the unusual and potentially harmful $CO_2$ presence in the inspiratory limb of the patient circuit. The computer will therefore, at the same time, increase the flow of fresh gas to the system to prevent recirculation of the expired gases into the inspiratory limb, thus suppressing the breakthrough of $CO_2$ gases and preventing those gases from being inhaled by the patient. The fresh gas flow is increased so that it exceeds the minute volume then being provided to the patient by the ventilator or other gas supplying means, that is, the increased flow of fresh gas must exceed the minute volume provided to the patient, preferable by a predetermined amount or ratio.

When the fresh gas flow rate is increased, the relative flow rates of the individual gases are adjusted by the computer to assure that the user set inspired gas and agent concentrations are maintained at the values set by the clinician. Further, if the increased flow of fresh gas is added to the inspiratory limb during inspiration such that the increase in gases alter the minute flows during inspiration, the inspired flow rate is compensated by the ventilator or other means.

In an alternate embodiment, although it is preferred that the increase of fresh gas flow not disturb the setting of concentration commanded by the user, the invention can be used in the absence of a computer controlled gas and agent delivery system with closed loop control that maintains the user setting of inspired gas and agent concentrations. Thus, the invention may be used where the user manually commands the desired gas flow rates and the vaporizer concentration setting. In such embodiment, if $CO_2$ breakthrough is detected by the gas monitor, the fresh gas flow is increased to prevent the expired gases from continuing to enter the inspiratory limb and thus suppress the breakthrough. The flow of gases are set such that the ratio of $O_2$ flow to the total fresh gas flow rate is delivered to the same ratio as the $O_2$ concentration measured in the inspiratory limb of the breathing circuit and the vaporizer is set at the lower value of the inspired agent concentration or the current vaporizer concentration setting. The remaining fresh gas is made up by the flow of the balance gas.

As in the preferred embodiment, an alarm can also be initiated to inform the clinician of the breakthrough condition, however, in such case, the clinician manually adjusts the commands to the gas flow rates and vapor concentration to maintain the desired concentration of gases and agent to the patient as needed.

Other objects, features and advantages of the present invention will be more apparent from the detailed description of the preferred embodiments set forth below, taken in conjunction with the accompanying drawings.

BRIEF DESCRIPTION OF THE DRAWINGS

The FIGURE is a block diagram of the components of an anesthesia system used to carry out the present invention.

DESCRIPTION OF THE PREFERRED EMBODIMENT

Figure 1:
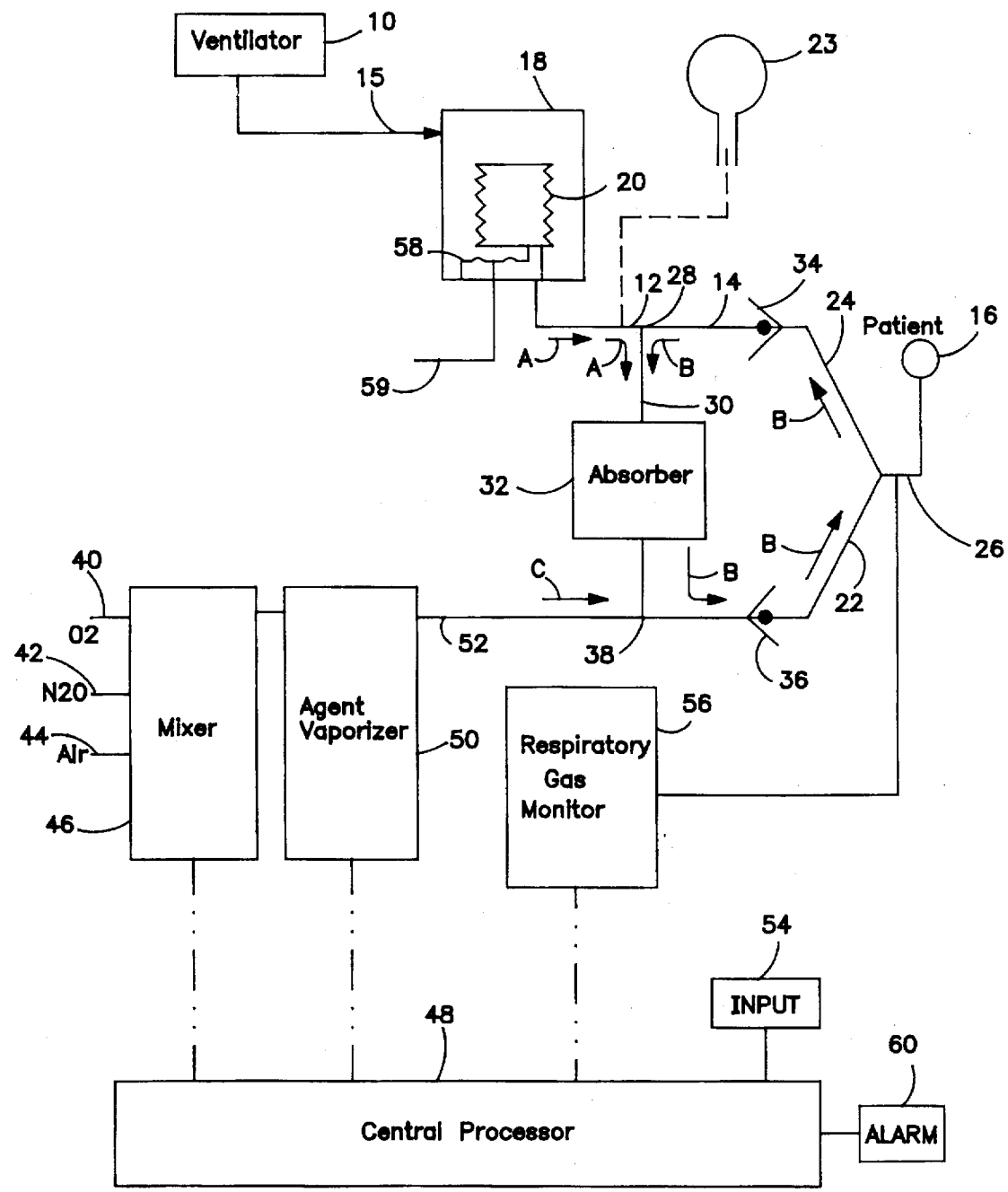

Referring now to the FIGURE, there is shown a block diagram of an anesthesia system adapted to carry out the subject invention. As shown, a ventilator 10 is provided and which may be of the type shown and described in U.S. Pat. No. 5,315,989 assigned to the present applicant and the disclosure of which is incorporated herein by reference. That ventilator 10 of the aforementioned U.S. Patent has an inhalation cycle and an exhalation cycle controlled by a central processing unit.

The ventilator 10 provides gas to the patient during the inhalation cycle via a conduit 12 to the patient breathing circuit 14 where it is delivered to the patient 16. The ventilator 10 typically includes a bellows assembly 18 and air or other powering gas is supplied to the bellows assembly 18 via conduit 15, exterior of the bellows 20 and which then collapses the bellows 20 to force gas within the bellows 20 to the patient 16. As will be described herein, the embodiment includes a ventilator 10 and bellows assembly 18, however, it will be understood that the present invention can be employed where the system is used in a critical care setting where a ventilator delivers the gas directly to the patient without the intervention of a bellows assembly as well as to the situation where the patient is being "bagged" by the clinician by means of breathing bag 23 or is carrying out spontaneous breathing and the patient is actually carrying out the breathing function but is connected to the breathing circuit.

As also noted in the aforementioned U.S. Patent, the patient breathing circuit 14 itself conventionally includes an inspiratory limb 22 and an expiratory limb 24 and the patient is connected to a wye connection 26 located intermediate the inspiratory and the expiratory limbs 22,24. The means of connection may be an endotracheal tube, face mask or other interface between the patient 16 and the patient breathing circuit 14.

In conventional operation, gas is delivered to the patient 16 by means of a powering gas from ventilator 10 that collapses the bellows 20 to drive the gas into conduit 12 and then into the tee 28 where the gas enters a conduit 30 and passes through an absorber 32. After passing through the absorber 32, the gas enters the inspiratory limb 22 of the patient breathing circuit 14 to be administered to the patient 16. As the patient exhales, that exhalation, now laden with $CO_2$, passes through the expiratory limb 24 where it again passes through the tee 28 and continues to the absorber 32 where the $CO_2$ is eliminated by a $CO_2$ absorbing material, such as sodalime.

A pair of check valves 34 and 36 are positioned in the patient breathing circuit 14 in the expiratory and inspiratory limbs 24 and 22, respectively, to maintain the flow of gas in the proper direction around the circle patient breathing circuit 14.

A flow of fresh gas is also introduced into the patient breathing circuit 14 and, as shown, is added at a tee 38 and thus into the inspiratory limb 22 of the patient breathing circuit 14. That flow of fresh gas is provided from a source of gas, typically oxygen and nitrous oxide to aid in anesthetizing the patient. As shown in the FIGURE, there is a supply of oxygen 40, nitrous oxide 42 and air 44 and such supply may be through a central piping system of a hospital or may be through the use of individual cylinders of such gases.

In any event, the gases are mixed in a gas mixer 46 in the proportion desired by the user. The actual control of the proportions and the flow through the gas mixer 46 is, in the preferred embodiment, controlled by a central processing unit (CPU) 48 as will be described. The mixed gas from the gas mixer 46 then passes through an agent vaporizer 50 where liquid anesthetic agent is vaporized and added to the stream of gas such that anesthetic laden gas continues into a conduit 52 and enters the patient breathing circuit 14 at the tee 38.

Again, in the preferred embodiment, the control of the agent vaporizer 50 is by means of the CPU 48 and which determines the percentage concentration of anesthetic agent that is in the gas that enters the patient breathing circuit 14 and thus that is supplied to the patient 16 to induce and maintain anesthesia.

The CPU 48 is, in turn, controlled by an input device 54 provided so that the clinician can input the data needed to determine the various parameters to provide the gas flow and anesthetic concentration desired to anesthetize the patient.

In the overall flow scheme of the present conventional system is therefor such that the gas in the bellows 20 is forced by the ventilator 10 into conduit 12 in accordance with the arrows A during the inhalation cycle of the patient 16. The gas thus passes through the tee 28 and through absorber 32 where it further passes through tee 38 and into the inspiratory limb 22 of the patient breathing circuit 14. At tee 38, fresh gas containing a predetermined concentration of an anesthetic agent is joined with the gas from the bellows 20 and proceeds with the gases already circulating in patient breathing circuit 14 and administered to the patient 16.

When the patient exhales, the exhaled gas passes through the expiratory limb 24 of the patient breathing circuit 14 through tee 28 and continue through the conduit 12 and into the bellows 20. At the same time, fresh gas that continuously flows into the circuit 14 from conduit 52 is also directed towards the bellows 20 after passing through the patient breathing circuit 14. When the bellows 20 reaches the end of its travel, any excess gas is popped off from the bellows 20 via pop-off valve 58 and exits the system via conduit 59.

During the inspiratory phase, the bellows 20 is driven downwardly by the ventilator 10. The unidirectional check valves 34 and 36 direct the gas from the bellows 20 to conduit 12 and through the absorber 32 where the gas is scrubbed of $CO_2$. Also directed is the fresh gas from conduit 52 towards the patient 16 via limb 22 of breathing circuit 14.

As can be seen, therefore, the anesthesia system is basically a circle system where the gas continues to pass in a circle as shown by the arrows B with the addition of fresh gas and the anesthetic agent added to that gas in the direction of Arrow C as the gas passes around the circle. Since the system is a closed system, it is also obvious that the absorber 32 is a necessary element to prevent the $CO_2$ that is exhaled by the patient 16 from continuing around the circle and entering the inspiratory limb 22 to be introduced into the patient 16. Since that is hazardous, it is important that the absorber 32 do its job of ridding the gas of $CO_2$ and that some protection be afforded in the event the absorber 32 is inadvertently not replaced when necessary, or is otherwise ineffective, and the $CO_2$ gas breaks through the absorber 32 into the inspiratory portion of the circle system.

As a further component of the overall anesthesia system, a gas monitor 56 is provided to detect certain gases in the inspiratory limb 22 and thus determine the actual gases that are introduced into the patient 16. Such gas analyzers conventionally detect oxygen, nitrous oxide, carbon dioxide and the anesthetic agent being used in the particular system.

The $O_2$ and agent inspired measurements of the analyzer 56 are provided to CPU 48 to compute the rate of gas flows and anesthetic vapor delivered by the gas mixer 46 and vaporizer 50, respectively, to maintain the user delivered inspired concentration set by the input 54. The feedback control algorithm to meet the user desired setting is secondary to this invention. In this case, the gas analyzer 56 also analyzes the concentration of $CO_2$ that can reach the patient 16. That $CO_2$ analysis is thus provided to the CPU 48.

In accordance with the present invention, therefore, when the gas monitor 56 recognizes the presence of $CO_2$ in the inspiratory limb 22, the information is conveyed to the CPU 48. The CPU 48 may take one or more steps to determine whether that finding of $CO_2$ in the inspiratory limb 22 is a deliberate action or is a $CO_2$ breakthrough in the system and therefore potentially harmful to the patient 16. One action the CPU 48 may take is to interrogate the gas mixer 46 to see if $CO_2$ has purposely been added to the system in the fresh gas stream through a source of $CO_2$ (not shown). Another action may be to determine if the absorber 32 has been deliberately bypassed via an absorber bypass switch(not shown). That interrogation may be by the CPU 48 simply determining the position of the absorber bypass switch.

If the CPU 48 determines that no deliberate action has occurred that would explain the presence of $CO_2$ in the inspiratory limb 22, it takes corrective action to alleviate the situation before harm can be caused to the patient 16.

To correct the breakthrough of $CO_2$ into the inspiratory limb 22, CPU 48 increases the flow of gas through the gas mixer 46 by sending an appropriate signal to the gas mixer 46. Since the increase in fresh gas flow alters the gas and agent concentration inspired by the patient 16, the CPU 48 recomputes the ratio of gases and vapor mixture in accordance with the feedback control algorithm mentioned earlier.

The increased gas flow rate must exceed the minute ventilation generated by the ventilator 10 or other means of supplying gas to the patient 16. The amount of increase can preferably be determined and established as a multiple of the minute ventilation, i.e. 1.2 times the minute ventilation as set or measured by the ventilator 10. Alternatively, the fresh gas flow can be gradually increased in steps of 1 liter/minute at every breath until the inspired $CO_2$ is no longer detected by the gas monitor 56.

The minute ventilation is basically the amount of gas delivered to the patient in a minute and, in the afore-described case where a ventilator is used, the value of minute ventilation is normally provided as a setting on the ventilator or a reading from the ventilator control panel. The minute volume may, however, readily be determined from standard monitors in the cases where a ventilator is not used, such as when the clinician is actually ventilating the patient be manipulating a bag, i.e. bagging the patient, or where the patient is spontaneously breathing the gas through his own effort from the patient breathing circuit. In the case of the bagging situation or spontaneous breathing, the minute volume is readily determined by ascertaining the tidal volume, that is, the volume of air inspired by the patient, and the breaths per minute inspired by the patient. Such measurements are generally available to the clinician and thus, the minute volume is derived by multiplying the tidal volume in liters per breath by the breaths per minute to arrive at liters per minute.

At the same time that the fresh gas flow is increased, the CPU 48 may signal the operator of the breakthrough condition by sending a signal to an alarm 60 to provide an aural and/or visual signal to the operator to advise of the $CO_2$ breakthrough condition.

As a further embodiment, where the control of the concentration of anesthetic vapor is a manual control, the present inventive system can still be employed such as to increase the flow of the fresh gas to back up flow from the absorber, however, where the vapor concentration is manually controlled, the unit merely activates the aural and/or visual alarm 60 to alert the clinician to the $CO_2$ breakthrough and the clinician thereafter makes whatever manual adjustment to the flow controllers in the anesthesia system are necessary to readjust the concentration of anesthetic agent introduced into the fresh gas to compensate for the increased flow of the fresh gas.

Thus, the increase of fresh gas acts to protect the patient from $CO_2$ but the clinician must take that increased flow into account and manually adjust the concentration to insure that the concentration of anesthetic to the patient stays at the desired setting.

While the present invention has been set forth in terms of a specific embodiment, it will be understood that the anesthesia system herein disclosed may be modified or altered by the those skilled in the art to other configurations. Accordingly, the invention is to be broadly construed and limited only by the scope and spirit of the claims appended hereto.

We claim:

1. An anesthesia system for providing anesthesia to a patient, comprising;

a substantially closed patient circuit adapted to be connected to the patient, said patient circuit having an inspiratory limb for introducing gases into the patient and an expiratory limb for receiving gases exhaled by the patient and wherein gases circulate through said patient circuit, check valve means in said patient circuit to allow flow within said circuit only in the direction from said expiratory limb into said inspiratory limb, an absorber in said substantially closed patient circuit for removing $CO_2$ from the gases circulating within said substantially closed patient circuit, means to supply a gas into said substantially closed patient circuit to provide a breath at a known minute volume to be delivered to the patient through said substantially closed patient circuit, means to introduce fresh anesthetic gas at a controllable flow rate into said substantially closed patient circuit at an inlet in said substantially closed patient circuit, a gas monitor to detect the presence of $CO_2$ in said inspiratory limb during the inspiratory phase of respiration, means responsive to the detection of $CO_2$ by said gas monitor to increase the flow rate of the fresh gas into said substantially closed patient circuit to a predetermined increased flow rate that exceeds the known minute volume of gas supplied to the patient, said increased flow of fresh gas effectively blocking the flow of gas from said expiratory limb into said inspiratory limb to suppress the passage of $CO_2$ from said expiratory limb into said inspiratory limb, and pop-off valve means located in said substantially closed patient circuit between the point where said expiratory limb receives gases from the patient and said inlet for the introduction of fresh gases into said substantially closed patient circuit to exhaust gases from said substantially closed patient circuit.

2. An anesthesia system as defined in claim 1 wherein said check valve means comprises a check valve located in said expiratory limb allowing flow of gas only in the direction from the patient and a check valve in said inspiratory limb allowing flow only toward the patient.

3. An anesthesia system as defined in claim 1 wherein said means to supply gas into said patient circuit comprises a mechanical ventilator.

4. An anesthesia system as defined in claim 1 wherein said means to supply gas into said patient circuit comprises a manually operable, flexible bag.

5. An anesthesia system as defined in claim 1 wherein said means to introduce fresh gas comprises a plurality of gas sources, a mixer for mixing the gases from said plurality of gas sources and a CPU controlling the mixer to determine the mixing and flow of such gases into said substantially closed patient circuit.

6. An anesthesia system as defined in claim 5 wherein said means to introduce fresh gas comprises an anesthetic vaporizer to introduce a controllable amount of anesthetic vapor into said flow of fresh gas and wherein said CPU controls said anesthetic vaporizer to control the concentration of anesthetic in said fresh gas flow.

7. An anesthesia system as defined in claim 6 wherein said CPU includes an input device operable by a user to set the desired flow rate of fresh gas from said mixer and the desired concentration of anesthetic agent introduced into said fresh gas flow by said anesthetic vaporizer and said CPU controls flow rate and anesthetic concentration to maintain the values set by the user by said input device.

8. An anesthesia system as defined in claim 7 wherein said CPU readjusts the flow rate of fresh gas from said mixer and the concentration of anesthetic agent from said anesthetic vaporizer upon the increase of flow to said predetermined increased flow rate to maintain said values set by the user in said input device.

9. An anesthesia system as defined in claim 5 wherein said CPU controls the increase of fresh gas by increasing the flow rate of fresh gas until said gas monitor no longer detects the presence of $CO_2$ in said inspiratory limb and maintaining said increased flow rate.

10. An anesthesia system as defined in claim 5 further including an alarm operable by said CPU to alert a clinician when said fresh gas flow is increased.

11. An anesthesia system for providing anesthesia to a patient comprising:

a substantially closed patient circuit adapted to be connected to the patient, said patient circuit having an inspiratory limb for introducing gases into the patient and an expiratory limb for receiving gases exhaled by the patient and wherein gases circulate through said patient circuit, check valve means in said patient circuit to allow flow within said circuit only in the direction from said expiratory limb into said inspiratory limb.

an absorber in said substantially closed patient circuit intermediate said expiratory limb and said inspiratory limb for removing $CO_2$ from the gases circulating within the system, gas supply means to provide a fresh gas into said patient circuit to supply a breathing gas mixture to the patient connected to said substantially closed patient breathing circuit at a known minute volume, fresh anesthetic gas supply means to introduce fresh gas at a controllable, predetermined flow rate into said substantially closed patient circuit, said fresh gas supply means having a gas mixer adapted to supply a gas of predetermined concentration into said substantially closed patient circuit and a vaporizer means adapted to introduce a predetermined quantity of an anesthetic vapor into said fresh gas flow, a central processing unit (CPU) for controlling the flow rate of the fresh gas from said mixer and for controlling the predetermined quantity of anesthetic vapor introduced into said fresh gas flow, a gas monitor to detect the presence of $CO_2$ in said inspiratory limb during the inspiratory phase of respiration and to signal said CPU upon detection of a predetermined amount of $CO_2$ in said inspiratory limb, said CPU signals said mixer to increase the flow rate of the fresh gas into said patient circuit in response to the detection of $CO_2$ by said gas monitor to a predetermined increased flow rate that exceeds the minute volume of gas being provided to the patient by said substantially closed breathing circuit, said increased flow of fresh gas blocking the flow of gas from said expiratory limb into said inspiratory limb to suppress the passage of $CO_2$ from said inspiratory limb into said inspiratory limb.

12. An anesthesia system for providing anesthesia to a patient as defined in claim 11 wherein said CPU further comprises an input device to provide a signal by a user of the desired anesthetic concentration and flow rate of gas to the patient and said CPU adjusts the flow of gas through said mixer and the concentration of anesthetic from said vaporizer to conform to the setting established by the user with said input device.

13. An anesthesia system for providing anesthesia to a patient as defined in claim 12 wherein said CPU readjusts the flow of said fresh gas and said concentration of anesthetic in said fresh gas after the flow rate of fresh gas has been increased.

14. An anesthesia system for providing anesthesia to a patient as defined in claim 11 further comprising an alarm to alert the user of the increased fresh gas flow and wherein said CPU provides a signal to activate said alarm.

15. An anesthesia system for providing anesthesia to a patient as defined in claim 11 wherein said gas supply means comprises a ventilator and wherein said ventilator provides a signal to said CPU indicative of the minute volume being provided to the patient by said ventilator.

\* \* \* \* \*